US010000534B2

(12) United States Patent
Chung et al.

(10) Patent No.: US 10,000,534 B2
(45) Date of Patent: Jun. 19, 2018

(54) PEPTIDE HAVING OSTEOBLAST PROLIFERATION ACTIVITY AND PERIODONTAL LIGAMENT FIBROBLAST PROLIFERATION ACTIVITY, AND USE OF SAME

(71) Applicant: CAREGEN CO., LTD., Anyang-si (KR)

(72) Inventors: Yong Ji Chung, Yongin-si (KR); Eun Mi Kim, Yongin-si (KR); Eung Ji Lee, Anyang-si (KR); A Reum Han, Icheon-si (KR); Hyun A Jung, Seoul (KR)

(73) Assignee: CAREGEN CO., LTD., Anyang-si (KR)

( * ) Notice: Subject to any disclaimer, the term of this patent is extended or adjusted under 35 U.S.C. 154(b) by 0 days. days.

(21) Appl. No.: 15/329,382

(22) PCT Filed: Aug. 5, 2014

(86) PCT No.: PCT/KR2014/007204
§ 371 (c)(1),
(2) Date: Jan. 26, 2017

(87) PCT Pub. No.: WO2016/017845
PCT Pub. Date: Feb. 4, 2016

(65) Prior Publication Data
US 2017/0247411 A1    Aug. 31, 2017

(30) Foreign Application Priority Data

Jul. 28, 2014   (KR) .................. 10-2014-0095893

(51) Int. Cl.
| *A61K 38/08* | (2006.01) |
| *A61K 38/21* | (2006.01) |
| *C07K 7/00* | (2006.01) |
| *C07K 7/04* | (2006.01) |
| *C07K 7/06* | (2006.01) |
| *A61K 38/00* | (2006.01) |

(52) U.S. Cl.
CPC ................ *C07K 7/06* (2013.01); *A61K 38/00* (2013.01)

(58) Field of Classification Search
None
See application file for complete search history.

(56) References Cited

U.S. PATENT DOCUMENTS 5,350,836 A * 9/1994 Kopchick .......... A01K 67/0275
435/69.4
5,516,891 A   5/1996 Siwruk et al.

2006/0211639 A1 * 9/2006 Bratzler .................. A61K 31/00
514/44 R
2012/0219511 A1 * 8/2012 Petropavlov ............ A61K 8/64
424/49
2012/0316118 A1   12/2012 Kang et al.

FOREIGN PATENT DOCUMENTS

| EP | 2383283 A2 | 11/2011 |
| JP | 2005-529585 | 10/2005 |
| JP | 2013-505972 A | 2/2013 |
| KR | 10-2009-0119718 A | 11/2009 |
| KR | 10-2009-0132506 A | 12/2009 |
| KR | 10-2010-0035240 A | 4/2010 |
| KR | 10-2011-0107552 A | 10/2011 |
| KR | 10-2012-0129127 A | 11/2012 |
| WO | WO-03/064600 A2 | 8/2003 |
| WO | WO-2007/049904 A1 | 5/2007 |
| WO | WO-2009/139525 A1 | 11/2009 |
| WO | WO-2009/154330 A1 | 12/2009 |
| WO | WO-2011/038754 A1 | 4/2011 |
| WO | WO-2011/105648 A1 | 9/2011 |

OTHER PUBLICATIONS

Tokuriki et al., 2009, Curr. Opin. Struc. Biol. 19:596-604.*
"Bone Diseases" (https://www.britannica.com/topic-browse/Health-and-Medicine/Diseases-and-Disorders/Bone-Diseases, accessed Oct. 16, 2017).*
Wiebe et al. (2000, J. Can. Dent. Assoc. 66:594-597).*
International Search Report dated Apr. 16, 2015 for International Application No. PCT/KR2014/007204, Chung et al., "Peptide Having Osteogenic Differentiation Promotion and Periodontal Ligament Fibroblast Activation Promotion, and Use of Same," filed Aug. 5, 2014 (10 pages).
Office Action dated Dec. 12, 2017 for Japanese Patent Application No. 2017-504365, Chung et al., "Peptide having osteogenic differentiation promotion and periodontal ligament fibroblast activation promotion, and use of same," filed Aug. 5, 2014 (7 pages).
Extended European Search Report dated Mar. 23, 2018 for European Patent Application No. 14898450.3, Yong Ji Chung et al., "Peptide having osteogenic differentiation promotion and periodontal ligament fibroblast activation promotion, and use of same," filed Aug. 5, 2014 (12 pages).

* cited by examiner

*Primary Examiner* — Elizabeth C. Kemmerer
(74) *Attorney, Agent, or Firm* — Clark & Elbing LLP; Susan M. Michaud

(57) ABSTRACT

A peptide comprising an amino acid sequence of SEQ ID NO: 1 or SEQ ID NO: 2, according to the present invention, shows proliferation and differentiation promotion of osteoblast and proliferation and activation promotion of periodontal ligament fibroblast. A peptide, according to the present invention, increases BMP signaling such as SMAD1/5/8 phosphorylation and increases the growth of osteoblast and the expression of a differentiation marker such as COL1A1, BSP and ALP, thereby ultimately showing osteoblast activation. A peptide, according to the present invention, promotes the growth of periodontal ligament fibroblast by means of PI3K and Akt phosphorylation and increases the expression of an activation marker such as COL1A1 and DSPP, thereby ultimately showing periodontal tissue regeneration activation. Provided are a composition for preventing or treating bone diseases and a composition for preventing or treating periodontal diseases, the compositions comprising the aforementioned peptide.

16 Claims, 15 Drawing Sheets

PEPTIDE HAVING OSTEOBLAST PROLIFERATION ACTIVITY AND PERIODONTAL LIGAMENT FIBROBLAST PROLIFERATION ACTIVITY, AND USE OF SAME

TECHNICAL FIELD

This application claims priority to and the benefit of Korean Patent Application No. 10-2014-0095893 filed in the Korean Intellectual Property Office on 28 Jul. 2014, the entire contents of which are incorporated herein by reference.

The present invention relates to a peptide having an osteogenic differentiation promoting ability and a periodontal ligament fibroblast activity promoting ability and a use thereof.

BACKGROUND ART

Bones are a common tissue calcified in our bodies and serve to support our bodies through a reforming procedure. The causes of bone diseases may be mainly divided into three: first, an abnormal size in the growth procedure; second, an imbalance between bone formation by osteoblasts and bone absorption by osteoclasts in the bone remodeling procedure; and third, abnormality in bone calcification or mineralization.

The transforming growth factor-beta (TGF-β) superfamily is composed of 40 or more members, such as Nodal, Activin, and bone morphogenetic proteins (BMPs). As for TGF-β signaling, particular types I and II serine/threonine kinase receptors form complexes, which penetrate plasma membranes through a form of a heteromeric complex to first transmit signals. TGF-β/BMPs are known to be involved in various functions in the body and bone formation of the mammalian development procedure. The disturbance of TGF-β/BMP signaling affects multiple bone-related diseases, such as tumor metastasis, phocomelia, and arthritis.

The bones of the body are a very dynamic organ such that the bones are gradually degraded every day, and the filling with new bones occurs by the amount of degraded bones, and thus, homeostasis is maintained. When the activity of one type cells between osteoclasts for degrading bones and osteoblasts for regenerating bones is increased or decreased, several diseases may be caused due to the destruction of homeostasis. The increase in activity of osteoclasts that absorb bones causes diseases, such as osteoporosis, in which the degradation of bones is promoted and the bones are thin and easily broken, and the increase in activity of the osteoblasts causes bone deformities or bone calcification due to increased bone density. Therefore, the balance between osteoclasts and osteoblasts is important.

As for drugs known until now, Korean Bone Bank, which is the Biosimilar pharmaceutical company, recently received approval for clinical test of "Rafugen" as a bone morphogenetic protein from Korean Food & Drug Administration and enter the clinical test thereof. Additionally, Daewoong released "Novosis" as a novel concept bio-fusion medical machine in which bone morphogenetic protein, "BMP2", is grafted on the artificial bones. The Novosis will be variously utilized in the bone graft-related treatment including implantation, in which the bones adhere better and the operation time and bleeding time decrease compared with auto-transplantation, and thus fast recovery is expected. Additionally, Dong-Wha Pharm released "DW1350", as a drug having excellent functions of inhibiting osteoclasts and promoting osteoblasts, but such a drug has been continuously subjected to clinical tests until now and is not released in Korea.

Throughout the entire specification, many papers and patent documents are referenced and their citations are represented. The disclosure of the cited papers and patent documents are entirely incorporated by reference into the present specification, and the level of the technical field within which the present invention falls and the details of the present invention are explained more clearly.

DETAILED DESCRIPTION OF THE INVENTION

Technical Problem

The present inventors endeavored to develop excellent peptides having effective biological activity, and as a result, the present inventors established that a peptide composed of an amino acid sequence of SEQ ID NO; 1 or SEQ ID NO; 2 has excellent biological activities, such as promoting growth and differentiation of osteoblasts and promoting activity of periodontal ligament fibroblasts, and thus completed the present invention.

Accordingly, an aspect of the present invention is to provide a peptide having an osteogenic differentiation promoting ability and a periodontal ligament fibroblast activity promoting ability.

Another aspect of the present invention is to provide a composition for preventing or treating bone diseases.

Still another aspect of the present invention is to provide a composition for preventing or treating periodontal diseases.

Other purposes and advantages of the present invention will become more obvious with the following detailed description of the invention, claims, and drawings.

Technical Solution

In accordance with an aspect of the present invention, there is provided a peptide having an osteogenic differentiation promoting ability, composed of one amino acid sequence selected from the group consisting of amino acid sequences of SEQ ID NO: 1 and SEQ ID NO: 2.

In accordance with an aspect of the present invention, there is provided a peptide having a periodontal ligament fibroblast promoting activity, composed of one amino acid sequence selected from the group consisting of amino acid sequences of SEQ ID NO: 1 and SEQ ID NO: 2.

The present inventors endeavored to develop excellent peptides having effective biological activity, and as a result, the present inventors established that a peptide composed of an amino acid sequence of SEQ ID NO; 1 or SEQ ID NO; 2 has excellent biological activities, such as promoting growth and differentiation of osteoblasts and promoting activity of periodontal ligament fibroblasts.

The peptides of the present invention include the amino acid sequence of SEQ ID NO: 1 or SEQ ID NO: 2. specifically, the peptides of the present invention are essentially composed of the amino acid sequence of SEQ ID NO: 1 or SEQ ID NO: 2.

According to an embodiment of the present invention, the peptide of the present invention promotes the proliferation of osteoblasts, induces the phosphorylation of Smad1, Smad5, and Smad8 to activate BMP signaling, and increases the expression of alkaline phosphatase (ALP), collagen type I alpha 1 (COL1A1), and bone sialoprotein (BSP), which are known as bone formation markers, ultimately promoting osteogenic differentiation.

According to another embodiment of the present invention, the peptide of the present invention promotes the growth of periodontal ligament fibroblasts through the phosphorylation of PI3K and Akt, increases the phosphorylation of PI3K and Akt, and increases the expression of active markers, such as collagen type I alpha 1 (COL1A1) and dentin sialophosphoprotein (DSPP) to promote the activity of periodontal ligament fibroblasts, ultimately exhibiting a periodontal regeneration activity.

As used herein, the term "peptide" refers to a linear molecule in which amino acid residues bind to each other via a peptide linkage. The peptide of the present invention may be prepared by chemical synthesis methods known in the art, especially, solid-phase synthesis techniques (Merrifield, J. Amer. Chem. Soc. 85:2149-54(1963); Stewart, et al., Solid Phase Peptide Synthesis, 2nd. ed., Pierce Chem. Co.: Rockford, 111(1984)) or liquid-phase synthesis techniques (U.S. Pat. No. 5,516,891).

According to an embodiment of the present invention, a protecting group, which is selected from the group consisting of an acetyl group, a fluorenyl methoxy carbonyl group, a formyl group, a palmitoyl group, a myristyl group, a stearyl group, and polyethylene glycol (PEG), may be linked to the N- or C-terminus of the peptide.

The foregoing amino acid modification significantly improves the stability of the peptides of the present invention. As used herein, the term "stability" refers to storage stability (e.g., room-temperature storage stability) as well as "in vivo" stability. The foregoing protecting group protects the peptides of the present invention from the attack of in vivo protein cleavage enzymes.

In accordance with another aspect of the present invention, there is provided a composition for preventing or treating bone diseases, the composition containing, as an active ingredient, one amino acid sequence selected from the group consisting of amino acid sequences of SEQ ID NO: 1 and SEQ ID NO: 2.

Since the composition of the present invention contains, as an active ingredient, the foregoing peptide composed of the amino acid sequence of SEQ ID NO: 1 or SEQ ID NO: 2 of the present invention, the descriptions of overlapping contents therebetween will be omitted to avoid excessive complexity of the present specification.

As validated in the following examples, the peptide composed of the amino acid sequence of SEQ ID NO: 1 or SEQ ID NO: 2 promotes the proliferation and differentiation of osteoblasts, and thus is very effective in the treatment or prevention of bone diseases.

The composition for preventing or treating bone diseases of the present invention can be used for all diseases occurring from a decrease in bone density due to an unsmooth osteoblastic function or from an excessive osteoclastic action due to inflammation of joints, and may be used for, for example, osteoporosis, boyhood osteoporosis, osteogenesis imperfecta, osteomalacia, osteonecrosis, rickets, osteomyelitis, alveolar bone loss, Paget's disease of bone, hypercalcemia, primary hyperparathyroidism, metastatic bone diseases, bone marrow, bone loss in rheumatoid arthritis, metastatic bone disease, cancer-related bone loss, fibrous dysplasia, adynamic bone disease, metabolic bone disease, and age-related bone mass loss.

According to one embodiment of the present invention, the composition of the present invention may be prepared into a pharmaceutical composition containing: (a) a pharmaceutically effective amount of the foregoing peptide of the present invention; and (b) a pharmaceutically acceptable carrier.

As used herein, the term "pharmaceutically effective amount" refers to an amount sufficient to attain efficacy or activity of the foregoing peptide.

The pharmaceutically acceptable carrier is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, and mineral oil. The pharmaceutical composition of the present invention may further contain, in addition to the above ingredients, a lubricant, a wetting agent, a sweetening agent, a flavoring agent, an emulsifier, a suspending agent, a preservative, and the like. Suitable pharmaceutically acceptable carriers and agents are described in detail in *Remington's Pharmaceutical Sciences* (19th ed., 1995).

The pharmaceutical composition of the present invention may be administered orally or parenterally, and examples of the parenteral administration may include intravenous, subcutaneous, intramuscular, intraperitoneal, local, and transdermal injections.

A suitable dose of the pharmaceutical composition of the present invention may vary depending on various factors, such as the method for formulation, the manner of administration, the age, body weight, gender, and morbidity of the patient, the diet, the time of administration, the excretion rate, and response sensitivity. Meanwhile, the dose of the pharmaceutical composition of the present invention is 0.0001-200 µg per day.

The pharmaceutical composition of the present invention may be formulated into a unit dosage form or a multidose container using a pharmaceutically acceptable carrier and/or excipient according to the method easily conducted by a person having ordinary skills in the art to which the present invention pertains. Here, the dosage form may be a solution in an oily or aqueous medium, a suspension, an emulsion, an extract, a powder, granules, a tablet, a capsule, or a gel (e.g., a hydrogel), and may further include a dispersant or a stabilizer.

In accordance with another aspect of the present invention, there is provided a composition for preventing or treating periodontal diseases, the composition containing, as an active ingredient, the foregoing peptide including one amino acid sequence selected from the group consisting of amino acid sequences of SEQ ID NO: 1 and SEQ ID NO: 2.

Since the composition of the present invention contains the foregoing peptide of the present invention as an active ingredient, the descriptions of overlapping contents therebetween will be omitted to avoid excessive complexity of the present specification.

The ultimate goal of periodontal disease treatment is to regenerate destroyed tissues in periodontal bones, periodontal ligament, cement, and the like. The human periodontal ligament fibroblasts can differentiate and proliferate into periodontal ligament fibroblasts, osteoblasts, cementoblasts, and thus play a pivotal role in the regeneration of the periodontal tissues, so that the human periodontal ligament fibroblasts are representative cells to be utilized in the application of periodontal tissue engineering for periodontal tissue regeneration. For the periodontal tissue regeneration, it is important to promote the proliferation of periodontal ligament cells having various differentiation abilities, thereby inducing the tissue regeneration.

As validated in the following examples, the peptide of the present invention promotes the proliferation and activity of periodontal ligament fibroblasts, thereby exhibiting enhancement effects of extracellular matrix components involved in the maintenance and regeneration of periodontal tissues. Therefore, the composition of the present invention is very effective in the prevention or treatment of various periodontal diseases.

The periodontal diseases are one type of numerous oral infectious diseases, and are main causes of tooth loss occurring in humans aged thirty or more. As used herein, the term "periodontal disease" includes numerous diseases that substantially influence the periodontium (periodontal tissue). The periodontal tissue is composed of covering structures and support structures, and includes alveolar bone, periodontal ligament, cementum, and gingival. A lot of other diseases influence tooth-supporting structures, while flock-induced inflammatory resin accounts for most of the periodontal diseases, and may be classified into gingivitis or periodontitis.

Herein, the periodontal diseases are selected from periodontitis, gingivitis, pericoronitis, parodontal abscess, periodontosis, other periodontal diseases, or a combination thereof.

As used herein, the term "gingivitis" refers to an inflammation in the gingival tissues, and a first cause of periodontal diseases. As used herein, the term "periodontitis" refers to inflammations occurring from alveolar bone, periodontal ligament, and cementum as well as a gingival unit. Generally, the periodontitis is characterized by a loss of chronic gingival attachment and radial bone loss.

The present invention may be provided in a form of an oral composition for the effective prevention and treatment of periodontal diseases, and the dosage form of the oral composition is not particularly limited, and may have an ordinary dosage form. Specifically, the oral composition may have a dosage form of a toothpaste, a mouthwash, or a mouth freshener. The oral composition provided in the present invention may contain various base agents and additives necessary for formulation depending on the dosage form thereof, and the kinds and amounts of these base agents and additives can be easily selected by a person skilled in the art. For example, when the dosage form of the oral composition is a toothpaste, an abrasive, a wetting agent, a foaming agent, a binder, a sweetener, a pH adjusting agent, a preservative, medicinal ingredients, a fragrance, a brightener, a pigment, a solvent, or the like may be added.

The composition for preventing or treating periodontal diseases of the present invention may be prepared into a pharmaceutical composition.

Advantageous Effects

Features and advantages of the present invention are summarized as follows:

(i) The peptide composed of the amino acid sequence of SEQ ID NO: 1 or SEQ ID NO: 2 of the present invention exhibits the effects of promoting the proliferation and differentiation of osteoblasts and promoting the proliferation and activity of periodontal ligament fibroblasts.

(ii) The peptide of the present invention increases BMP signaling, such as smad1/5/8 phosphorylation, thereby increasing the growth of osteoblasts and the expression of differentiation markers, such as COL1A1, BSP, and ALP, ultimately exhibiting osteogenic activity.

(iii) The peptide of the present invention promotes the growth of periodontal ligament fibroblasts through the phosphorylation of PI3K and Akt and increases the expression of activation markers, such as COL1A1 and DSPP, thereby ultimately exhibiting periodontal tissue regeneration activity.

(iv) The present invention provides a composition for preventing or treating bone diseases containing the foregoing peptide and a composition for preventing or treating periodontal diseases containing the foregoing peptide.

MODE FOR CARRYING OUT THE INVENTION

Figure 1A:
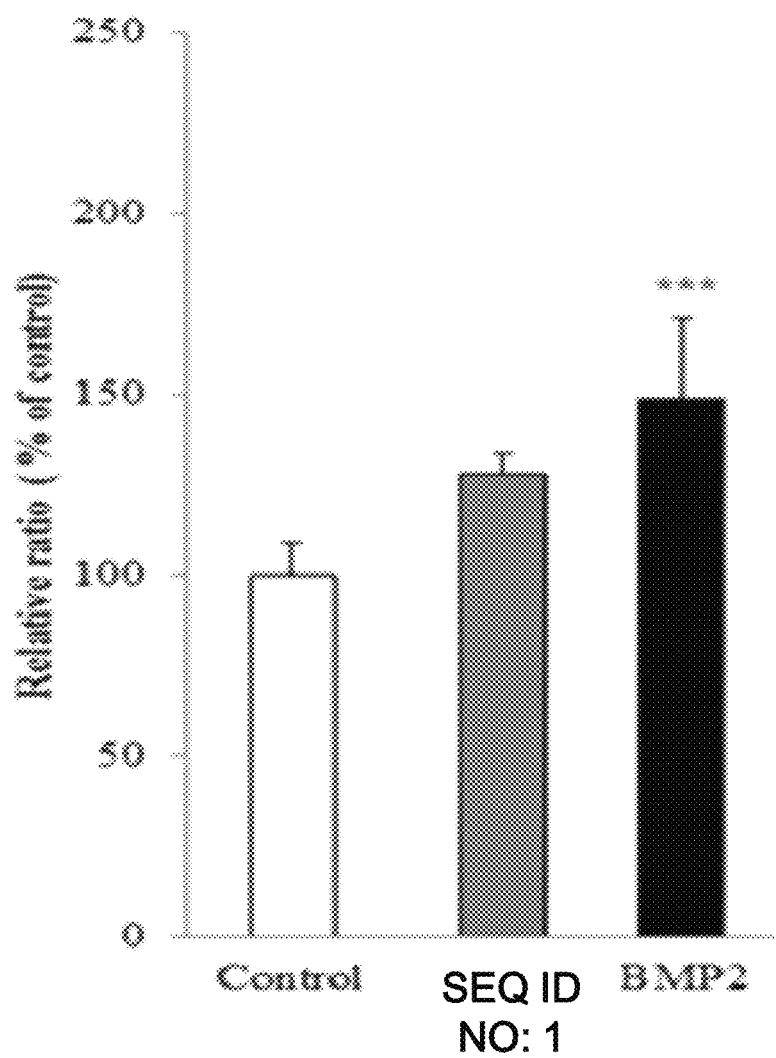
FIG. 1a is a graph showing a growth promotion effect of osteoblasts treated with the peptide of SEQ ID NO: 1 prepared by a synthesis example of the present invention.

Hereinafter, the present invention will be described in detail with reference to examples. These examples are only for illustrating the present invention more specifically, and it will be apparent to those skilled in the art that the scope of the present invention is not limited by these examples.

EXAMPLES

Synthesis Example 1: Peptide Synthesis 700 mg of chloro trityl chloride resin (CTL resin, Nova Biochem Cat No. 01-64-0021) was put into a reaction container, and 10 ml of methylene chloride (MC) was added, followed by stirring for 3 minutes. After the solution was removed, 10 ml of dimethylform amide (DMF) was added, followed by stirring for 3 minutes, and then the solvent was again removed. 10 ml of a dichloromethane (DCM) solution was put into the reactor, and 200 mmole Fmoc-Ser(tBu)-OH (Bachem, Swiss) and 400 mmole diisopropyl ethylamine (DIEA) were added, after which the mixture was well dissolved with stirring, and then the reaction was washed with stirring for 1 hour. After the reaction, the reaction product was washed, and then methanol and DIEA (2:1) were dissolved in DCM, followed by reaction for 10 minutes, and then the reaction product was conducted using excessive DCM/DMF (1:1). After the solution was removed, 10 ml of DMF was added, followed by stirring for 3 minutes, and then the solvent was again removed. 10 ml of a deprotection solution (20% piperidine/DMF) was put into the reactor, followed by stirring at room temperature for 10 minutes, and then the solution was removed. An equal amount of a deprotection solution was added, and then the reaction was again maintained for 10 minutes, followed by removal of the solution. Then, the reaction product was washed twice with DMF, once with MC, and once with DMF, for 3 minutes each, thereby preparing Ser (tBu)-CTL Resin.

10 ml of a DMF solution was put in a new reactor, and 200 mmol Fmoc-Lys(Boc)-OH (Bachem, Swiss), 200 mmol HoBt, and 200 mmole Bop were added, and the mixture was well dissolved with stirring. 400 mmole N,N-diisopropyl-ethylamine (DIEA) was divisionally put twice into the reactor, and then the stirring was conducted for at least 5 minutes until all solids were dissolved. The dissolved amino acid mixed solution was put in a reaction container containing the deprotected resin, and the reaction was conducted with stirring at room temperature for 1 hour. After the reaction liquid was removed, the stirring was conducted using a DMF solution three times for 5 minutes each, followed by removal. A small amount of the reacted resin was taken to check the reaction degree by the Kaiser test (Ninhydrin test). Using the deprotection solution, the deprotection reaction was conducted twice in the same manner as described above, thereby preparing Lys(Boc)-Ser(tBu)-CTL Resin. After sufficient washing with DMF and MC, the Kaiser test was again conducted, and then the following amino acid attachment test was conducted in the same manner as described above.

Based on the selected amino acid sequence, the chain reaction was conducted in the order of Fmoc-Gln(Trt), Fmoc-Ser(tBu), Fmoc-Asp(OtBu), Fmoc-Arg(Pbf), Fmoc-Leu, Fmoc-Asn(Trt), Fmoc-Leu, Fmoc-Ser(tBu), Fmoc-Arg(Pbf). The Fmoc-protecting group was removed by reaction twice with the deprotection solution for 10 min for each, followed by removal through well washing. Acetic anhydride, DIEA, and hydroxy benzotriazole (HoBt) were added to conduct acetylation for 1 hour, and then the prepared peptidyl resin was washed three times sequentially with DMF, MC, and methanol, dried under the flow of nitrogen gas, and completely dried by vacuum-drying under phosphorus pentoxide ($P_2O_5$). 30 ml of a leaving solution [95% trifluoroacetic acid (TFA), 2.5% distilled water, and 2.5% thioanisole] was added, and the reaction was maintained for 2 hours while the mixture was intermittently stirred at room temperature. The resin was filtered, washed with a small amount of a solution, and then mixed with stock solution. The distillation was conducted under reduced pressure to reduce the total volume by half, and then 50 ml of cold ether was added to induce precipitation. Thereafter, the precipitates were collected by centrifugation, followed by washing twice with cold ether. The stock solution was removed, followed by sufficient drying under nitrogen atmosphere, thereby synthesizing 0.85 g of unpurified peptide 1, Arg-Ser-Leu-Asn-Leu-Arg-Asp-Ser-Gln-Lys-Ser (yield: 89.9%). The molecular weight was determined as 1303 (theoretical value: 1303.440) by using a molecular weight analysis system. Peptide 2, Phe-Asp-Met-Gly-Ala-Tyr-Lys-Ser-Ser-Lys (SEQ ID NO: 2), was also synthesized by the same method (yield: 92.1%). The molecular weight was determined as 1133 (theoretical value: 1133.275) by using a molecular weight analysis system.

TABLE 1

| SEQ ID NO | Amino acid sequence | Analysis value (Mass spectrometer) | |
|---|---|---|---|
| | | Analysis value | Theoretical value |
| 1 | Arg-Ser-Leu-Asn-Leu-Arg-Asp-Ser-Gln-Lys-Ser | 1303 | 1303.440 |
| 2 | Phe-Asp-Met-Gly-Ala-Tyr-Lys-Ser-Ser-Lys | 1133 | 1133.275 |

Example 1: Verification on Osteocytes Growth Effect Using Synthetic Peptides

In order to analyze the BMP2-like action of the sequence peptides synthesized in synthesis example 1, MTT assay was conducted using C2C12 cells, which are a myoblast cell line, to investigate the proliferation promoting effect.

The C2C12 cells were cultured in Dulbecco's modified Eagle's medium (DMEM, Gibco) supplemented with 10% fetal bovine serum (FBS, Sigma) using a 500 ml-flask for tissue culture. The cultured cell lines were carefully detached from the bottom of the culture container using a 1% trypsin solution, followed by centrifugation, thereby obtaining only cell precipitates. The cell precipitates were re-suspended in DMEM culture medium supplemented without FBS, and then added to a 96-well plate for tissue culture at $1 \times 10^3$ cells per each well, followed by culture under conditions of 37° C. and 5% CO₂ for 24 hours. After 24 hours, the medium was changed with the same culture liquid completely excluding serum, and then the blank sample and each of the synthetic peptide were dissolved sterile in distilled water, and the mixture was cultured at a concentration of 10 μg/ml for 72 hours under the same conditions. The MTT sample was added to the culture-completed well, and after 4 hour, the formed formazan was dissolved in DMSO, and then the absorbance was measured at 560 nm to determine cell proliferation.

Figure 1B:
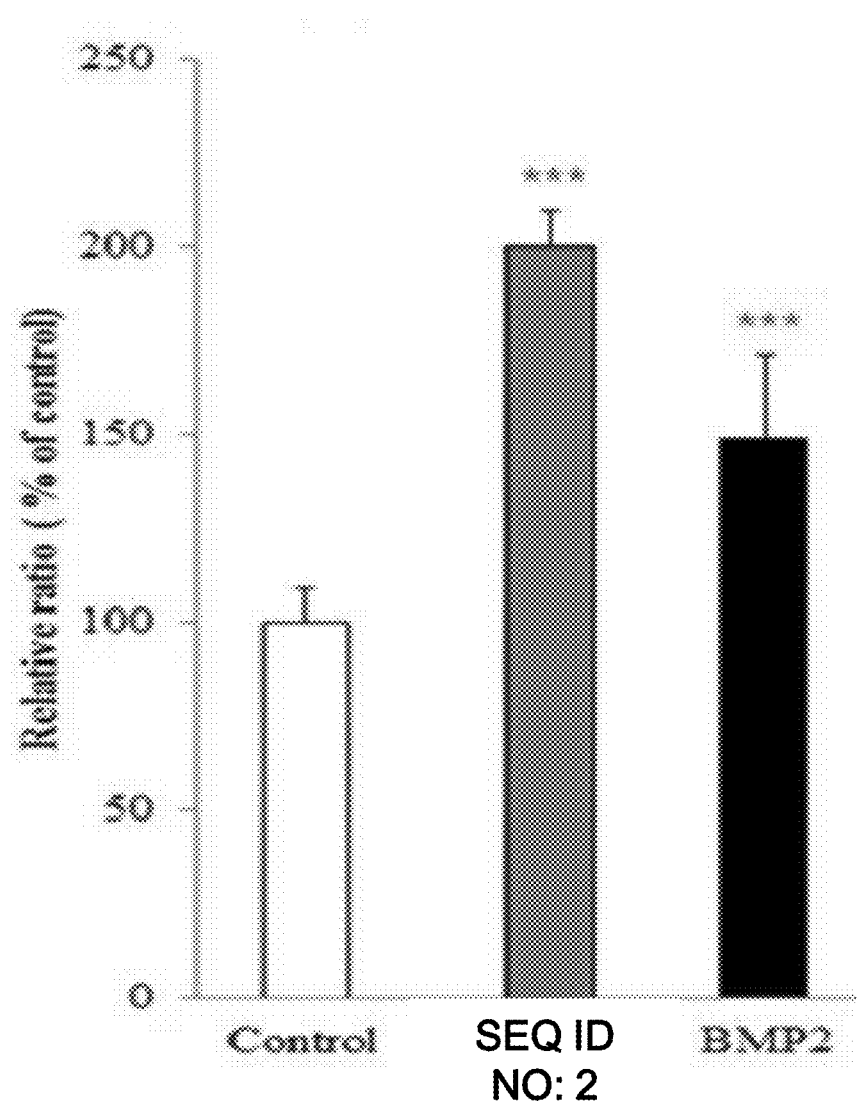
FIG. 1b is a graph showing a growth promotion effect in osteoblasts treated with the peptide of SEQ ID NO: 2 prepared by a synthesis example of the present invention.

FIG. 1 illustrates results of osteoblasts growth after the treatment with the peptides of SEQ ID NO: 1 and SEQ ID NO: 2. As shown in FIGS. 1a and 1b, the peptides of the present invention significantly promoted the growth of osteoblasts.

The peptides of the present invention were found by binding with the BMP Ib type receptor, and it was verified that the present peptide played the same role as BMP, which is a protein that is important in the formation of bones. The BMP receptor Ib type binding peptide of the present invention performs a similar function to natural BMP.

Example 2: Verification on Osteogenic Differentiation Promoting Effect of Synthetic Peptides In order to analyze the BMP2-like action of the sequence peptides synthesized in synthesis example 1, the osteoblast differentiation promoting effect was investigated through alkaline phosphatase (ALP) staining of MC3T3-E1 cells, which are a pre-osteoblast cell line. The MC3T3-E1 cells were placed in a 24-well plate to 3×10⁴ cells, and then cultured for 24 hours under conditions of 37° C. and 5% CO₂. After 24 hours, the alpha-MEM medium containing 10% FBS and 50 ug/ml ascorbic acid+100 mM b-glycerophosphate was treated with the synthetic peptides at concentrations of 10 ug/ml and 50 ug/ml, and then the culture was conducted for 13 days while the medium was exchanged every three days. The culture-completed plate well was washed two times with PBS, and then the cells were immobilized with an immobilization buffer, in which acetone, 37% formaldehyde, and citric acid solution were mixed, for 30 seconds. The following staining was carried out using the leukocyte alkaline phosphatase staining kit (SIGMA).

The cells were treated for 2 minutes with an FBB-alkaline solution and a sodium nitrite solution mixed at 1:1, and then treated with a buffer composed of distilled water and naphthol AS-BI alkaline solution, followed by color development in an incubator at 37° C. for 1 hour.

Figure 2A:
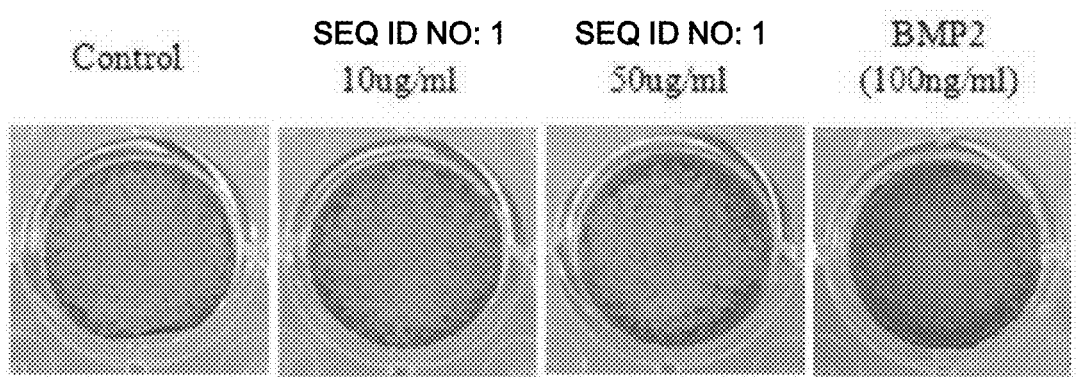
FIG. 2a illustrates results verifying the expression level of alkaline phosphatase (ALP) in the treatment with the peptide of SEQ ID NO: 1 prepared by the synthesis example of the present invention.
Figure 2B:
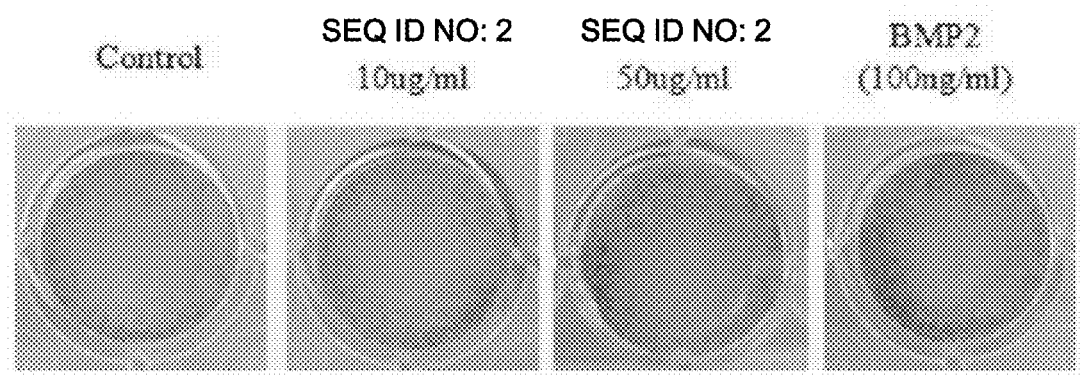
FIG. 2b illustrates results verifying the expression level of alkaline phosphatase (ALP) in the treatment with the peptide of SEQ ID NO: 2 prepared by the synthesis example of the present invention.

As results of testing, when pre-osteoblasts MC3T3-E1 were treated with the peptides of SEQ ID NO: 1 and SEQ ID NO: 2 at different concentrations, the increase in the ALP expression according to the promotion of differentiation was verified (FIGS. 2a and 2b).

Example 3: Verification on Increases in Expression of Osteogenic Differentiation-Related Genes by Synthetic Peptides In order to investigate the mRNA expression levels of osteogenic differentiation-related genes, bone sialoprotein (BSP) and collagen type I alpha 1 (COL1A1) by the sequence peptides synthesized in synthesis example 1, MC3T3-E1 cells were placed in a 6-well plate to 2×10⁵ cells, and then cultured for 24 hours under conditions of 37° C. and 5% CO₂. After 24 hours, the medium containing FBS 10% was treated with the respective peptides at 10 ug/ml and 50 ug/ml, and BMP2 used at a positive control at 100 ng/ml. After 2 days, the washing was conducted with PBS, and then RNA was isolated using Easy blue (Intron). cDNA was synthesized using 1 ug of RNA and RT premixture (Intron), and PCR was conducted using PCR premixture (Bioneer), and then the resulting product was loaded on agarose gel to investigate the mRNA expression degree of each gene.

Figure 3A:
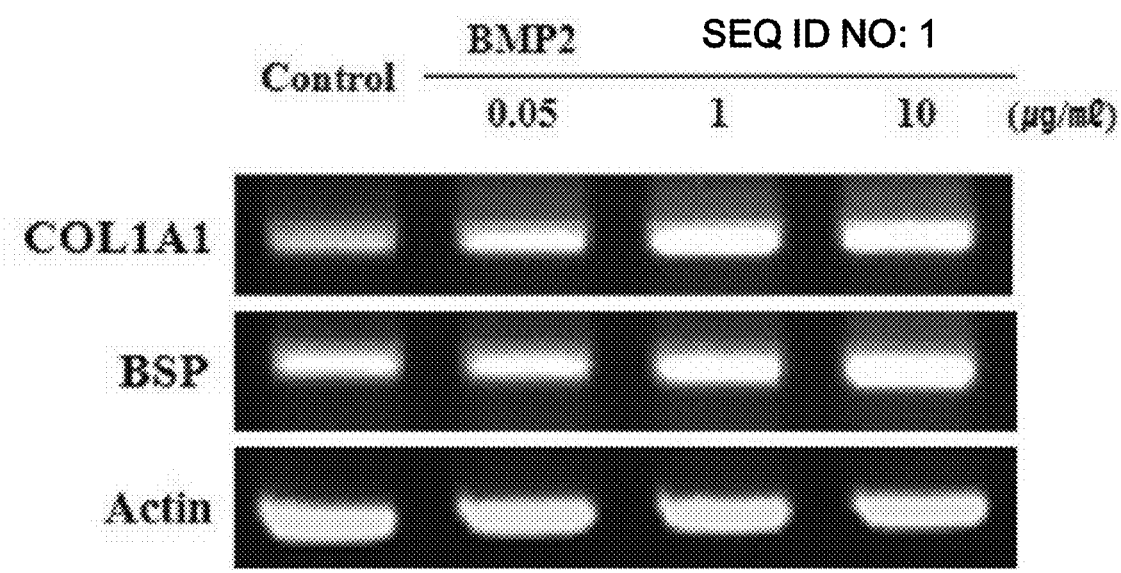
FIG. 3a illustrates results verifying mRNA expression levels of osteogenic differentiation markers in the treatment with the peptide of SEQ ID NO: 1 prepared by the synthesis example of the present invention.
Figure 3B:
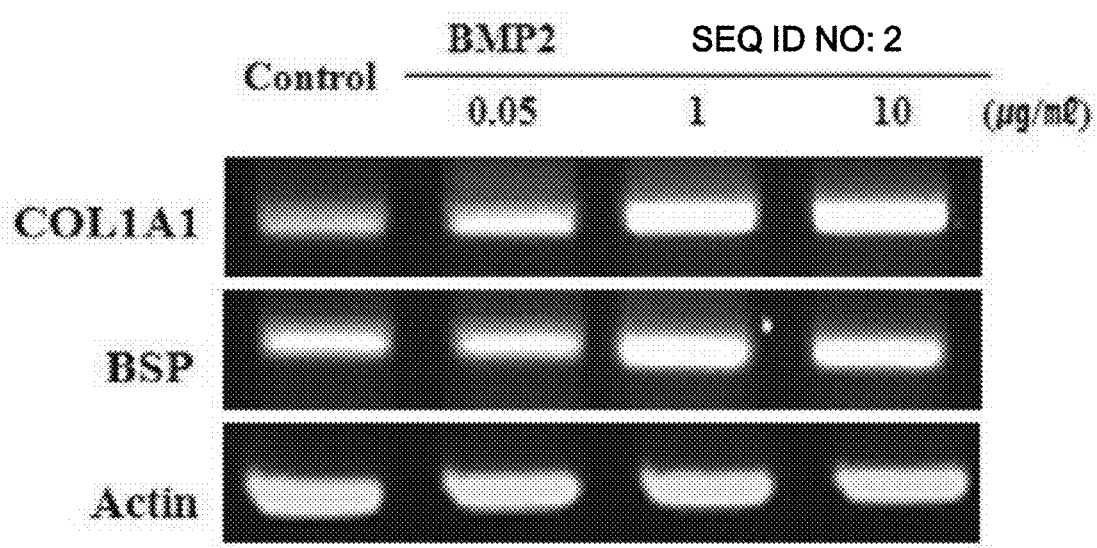
FIG. 3b illustrates results verifying mRNA expression levels of osteogenic differentiation markers in the treatment with the peptide of SEQ ID NO: 2 prepared by the synthesis example of the present invention.

As results of testing, when pre-osteoblasts MC3T3-E1 were treated with the peptides of SEQ ID NO: 1 and SEQ ID NO: 2 at different concentrations, the increases in the mRNA expression levels of the osteogenic differentiation genes were verified (FIGS. 3a and 3b).

Example 4: Verification on Osteogenic Differentiation Signal Promotion Effect by Synthetic Peptides In order to investigate whether pSmad1/5/8, which is a signal involved in the promotion of osteogenic differentiation, was activated by the present peptides, MC3T3-E1 cells were placed in a 6-well plate at 2×10⁵ cells, and then cultured for 24 hours under the conditions of 37° C. and 5% CO₂. After 24 hours, the medium was exchanged with a medium without serum, followed by culture for 24 hours. Then, the resulting product was treated with the respective peptides at 10 ug/ml, and BMP2 used at a positive control at 50 ng/ml. After 15 minutes and 30 minutes, the washing was conducted with PBS, and then a lysis buffer was added to obtain proteins through lysis, followed by western blotting.

Figure 4A:
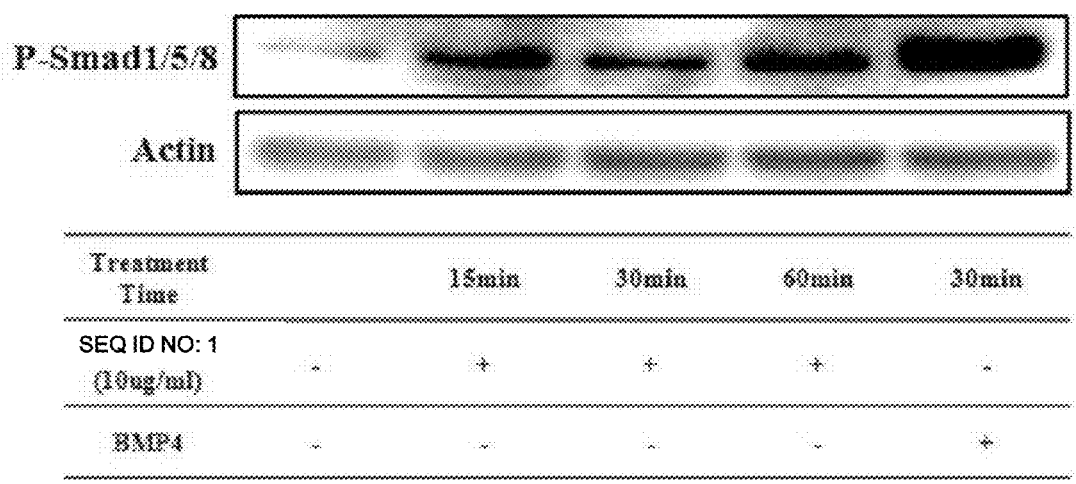
FIG. 4a illustrates results verifying the phosphorylation level of Smad1/5/8 as an osteogenic differentiation-related signal in the treatment with the peptide of SEQ ID NO: 1 prepared by the synthesis example of the present invention.
Figure 4B:
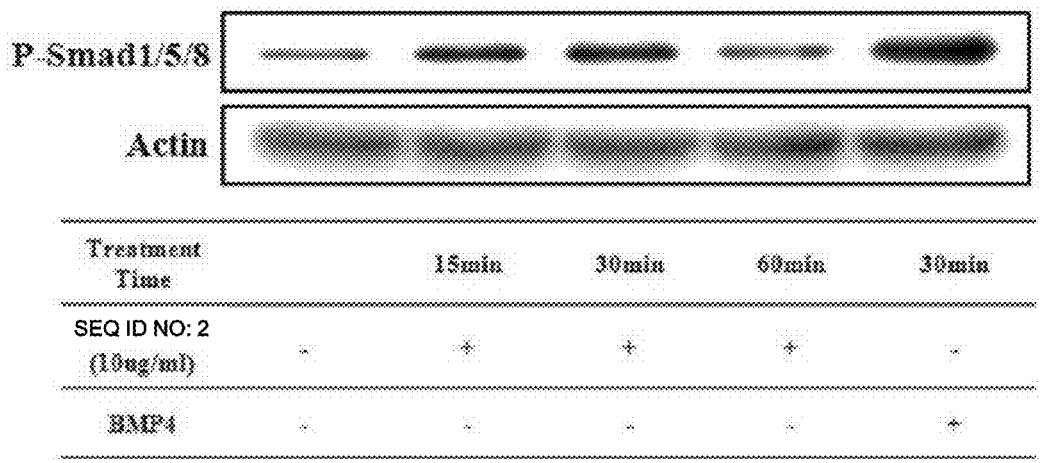
FIG. 4b illustrates results verifying the phosphorylation level of Smad1/5/8 as an osteogenic differentiation-related signal in the treatment with the peptide of SEQ ID NO: 2 prepared by the synthesis example of the present invention.

As results of testing, when pre-osteoblasts MC3T3-E1 were treated with the peptides of SEQ ID NO: 1 and SEQ ID NO: 2 at different concentrations, the promotion of the phosphorylation of Smad1/5/8 exhibiting the osteogenic differentiation signal activation was verified (FIGS. 4a and 4b).

Figure 5:
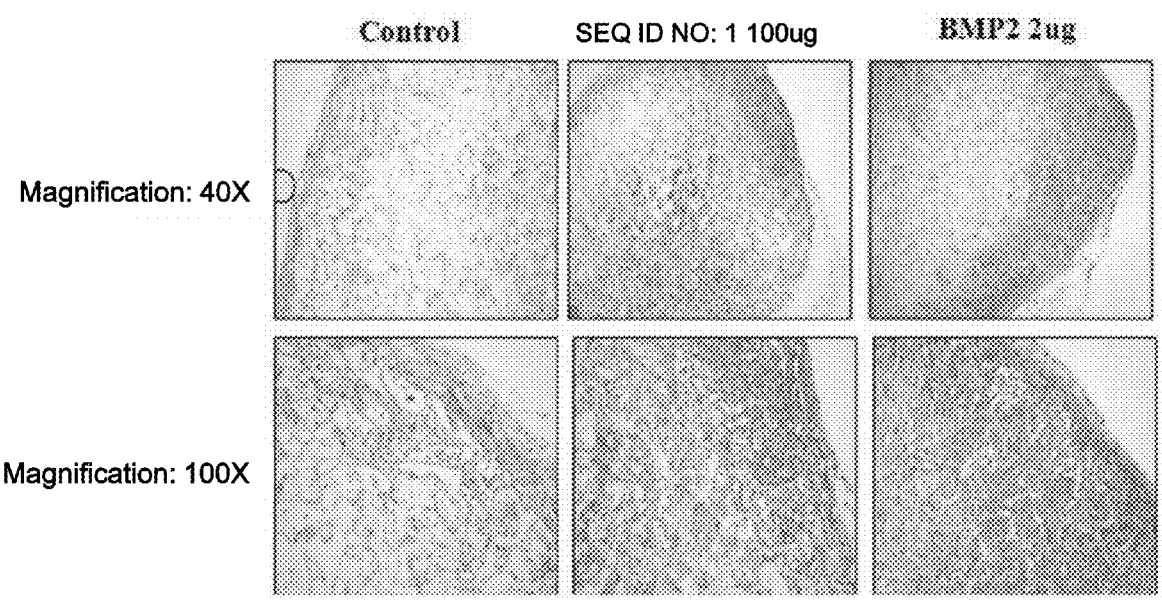
FIG. 5 illustrates H&E staining results verifying aspects of osteocytes penetrating into collagen sponges in the treatment with the peptide of SEQ ID NO: 1 prepared by the synthesis example of the present invention.

Example 5: Verification on Osteocytes Permeation and Proliferation Effect by Synthetic Peptides A collagen sponge with a size of 0.5 mm×0.5 mm was wetted with 100 ug of the peptide of SEQ ID NO: 1, transplanted into the back of the Balb/c mouse, and then left for 2 weeks. Thereafter, the collagen sponge was extracted, and then made into a paraffin block, and then the degree of osteocytes permeation and differentiation in the collagen sponge were measured through H&E staining (FIG. 5).

Through the results, the bone formation promoting effect, such as osteocytes proliferation and differentiation, of the peptide of SEQ ID NO: 1, which have been shown in vitro, was again verified in vivo.

Example 6: Verification on Periodontal Ligament Fibroblast Growth Promoting Effect by Synthetic Peptides In order to investigate the effects of the peptides of SEQ ID NO: 1 and SEQ ID NO: 2 on the periodontium, the human periodontal ligament fibroblast promoting effects were analyzed. The periodontal ligament fibroblasts were placed in a 48-well plate to 1×10³ cells, and then cultured for 24 hours under conditions of 37° C. and 5% CO₂. After 24 hours, the exchange with the medium not containing serum was conducted, followed by culture for 6 hours. Thereafter, the resulting product was treated with the peptides at concentrations of 0.05-10 ug/ml and BMP-2 and IGF-1 used as positive controls at a concentration of 0.2 ug/ml, followed by culture for 72 hours. After the completion of the culture, the culture supernatant was removed and the cells were immobilized using ethanol. After the cell immobilization was ended, the cells were washed three times with phosphate buffer saline (PBS). After the wash solution was removed, the cells were treated with colorimetric SRB solution, and sufficiently washed with 1% acetic acid. Then, the cells were observed using a microscope to observe the conditions of living cells. The absorbance for the solution decolorized with 20 mM tris was read at UV light of 560 nm, thereby measuring the survival conditions of cells.

Figure 6A:
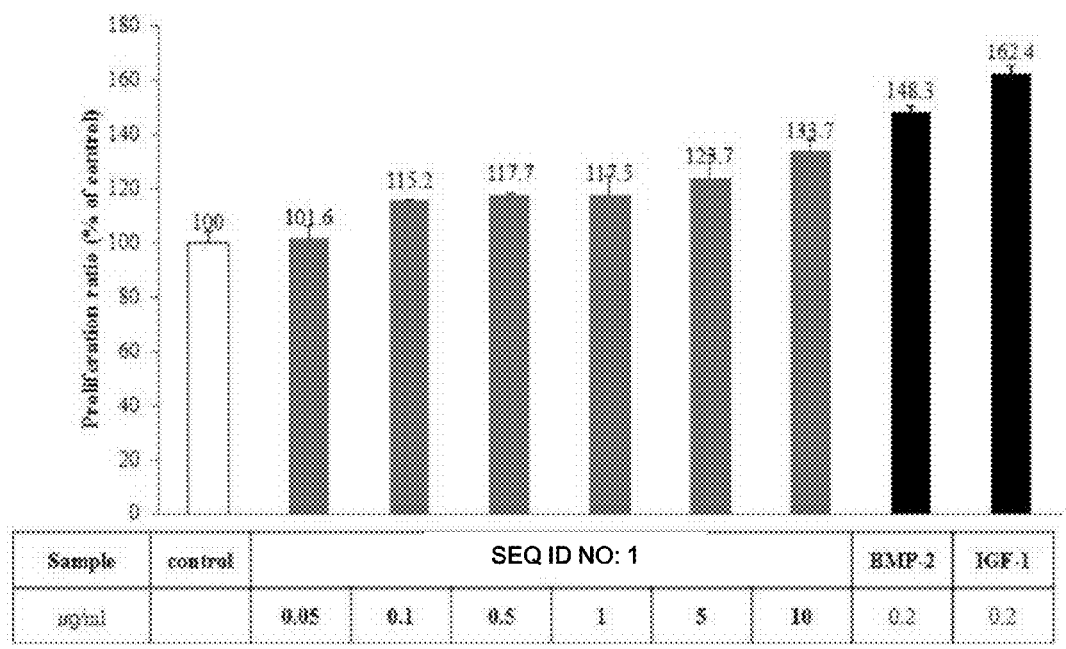
FIG. 6a is a graph showing a growth promotion effect of periodontal ligament fibroblasts treated with the peptide of SEQ ID NO: 1 prepared by a synthesis example of the present invention.
Figure 6B:
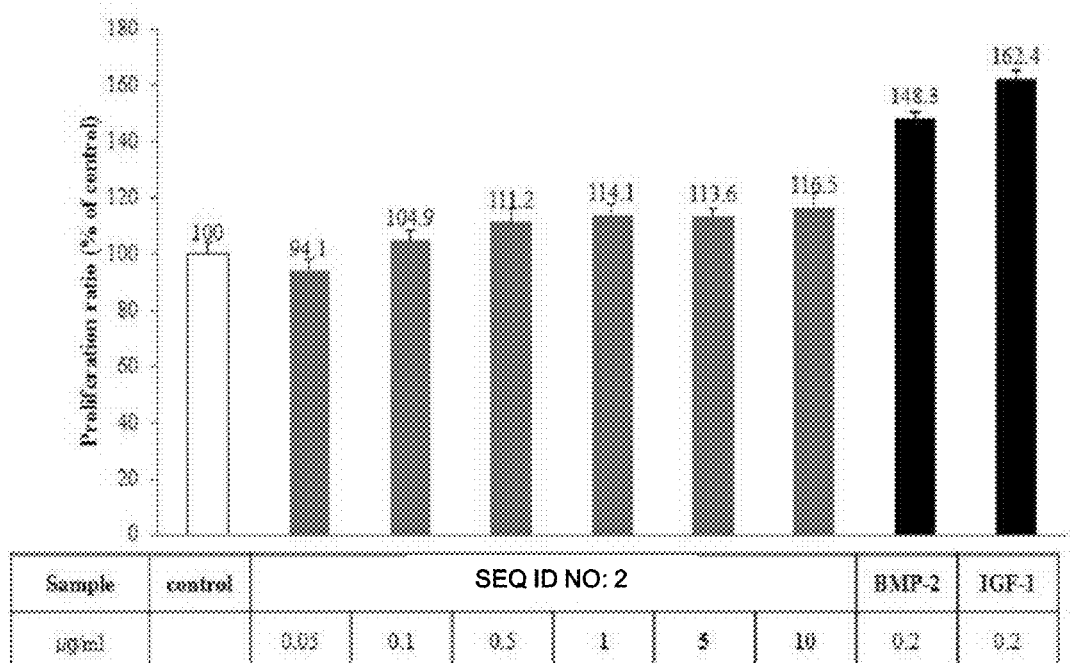
FIG. 6b is a graph showing a growth promotion effect of periodontal ligament fibroblasts treated with the peptide of SEQ ID NO: 2 prepared by a synthesis example of the present invention.

As results of testing, when the periodontal ligament fibroblasts were treated with the peptides of SEQ ID NO: 1 and SEQ ID NO: 2 at different concentrations, the cell growth increase in a dose-dependent manner was verified (FIGS. 6a and 6b).

Example 7: Verification on Periodontal Ligament Fibroblast Growth Promoting Mechanism by Synthetic Peptides In order to investigate the human periodontal ligament fibroblast growth promoting effects by the peptides of SEQ ID NO: 1 and SEQ ID NO: 2, the phosphorylation degrees of related signaling molecules were analyzed using western blotting. The periodontal ligament fibroblasts were placed in a 6-well plate to $5 \times 10^5$ cells, and then cultured for 24 hours under conditions of 37° C. and 5% $CO_2$. Thereafter, the resulting product was treated with the peptides at a concentration of 10 ug/ml and bFGF used as a positive control at a concentration of 0.2 ug/ml. Then, the cells were collected by culture times of 5-15 minutes, and the total proteins were isolated, and then western blotting was conducted with respect to p-PI3K and p-Akt.

Figure 7A:
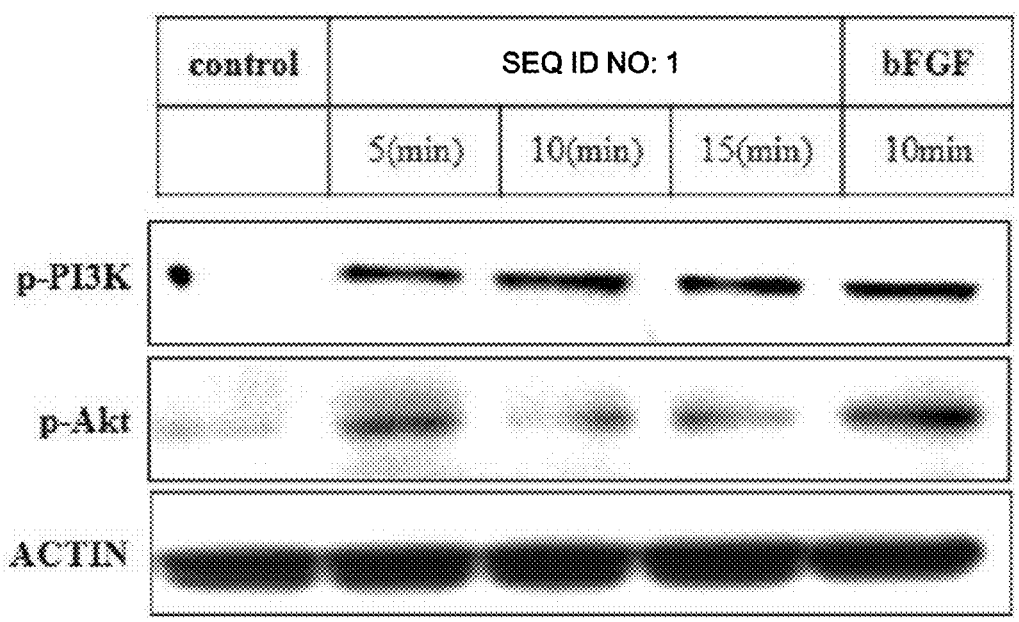
FIG. 7a illustrates results verifying the increases in phosphorylation levels of PI3K and Akt, which are proteins related to the growth promotion of periodontal ligament fibroblasts in the treatment with the peptide of SEQ ID NO: 1 prepared by a synthesis example of the present invention.
Figure 7B:
FIG. 7b illustrates results verifying the increases in phosphorylation levels of PI3K and Akt, which are proteins related to the growth promotion of periodontal ligament fibroblasts in the treatment with the peptide of SEQ ID NO: 2 prepared by a synthesis example of the present invention.

As results of testing, when the periodontal ligament fibroblasts were treated with the peptides of SEQ ID NO: 1 and SEQ ID NO: 2, the increases in the phosphorylation levels of PI3K and Akt were verified (FIGS. 7a and 7b).

Example 8: Verification on Periodontal Ligament Fibroblast Activity Promoting Effect by Synthetic Peptides In order to investigate the periodontal ligament fibroblast activity promoting effects by the peptides of SEQ ID NO: 1 and SEQ ID NO: 2, the mRNA expression of related genes was analyzed using RT-PCR. The periodontal ligament fibroblasts were placed in a 24-well plate to $1.5 \times 10^4$ cells, and then cultured for 24 hours under conditions of 37° C. and 5% $CO_2$. After 24 hours, the exchange with the medium not containing serum was conducted, followed by culture for 24 hours. Thereafter, the resulting product was treated with the peptides at concentrations of 1 and 10 ug/ml and BMP-2 and IGF-1 used as positive controls at a concentration of 0.2 ug/ml, followed by culture for 72 hours. After the completion of the culture, the washing was conducted with PBS, and then RNA was isolated using Easy blue (Intron). cDNA was synthesized using 1 ug of RNA and RT premixture (Intron), and PCR was conducted using PCR premixture (Bioneer), and then the resulting product was loaded on agarose gel to investigate the mRNA level of each marker.

Figure 8A:
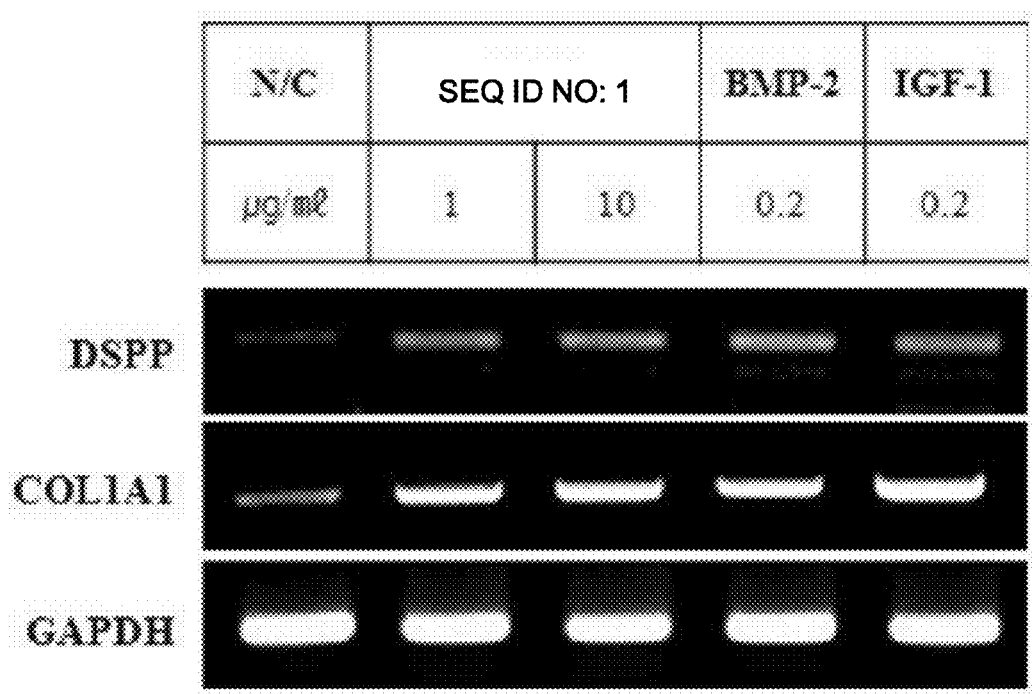
FIG. 8a illustrates results verifying the increases in mRNA expression levels of COL1A1 and DSPP, which are genes related to the activation of periodontal ligament fibroblasts, in the treatment with the peptide of SEQ ID NO: 1 prepared by a synthesis example of the present invention.
Figure 8B:
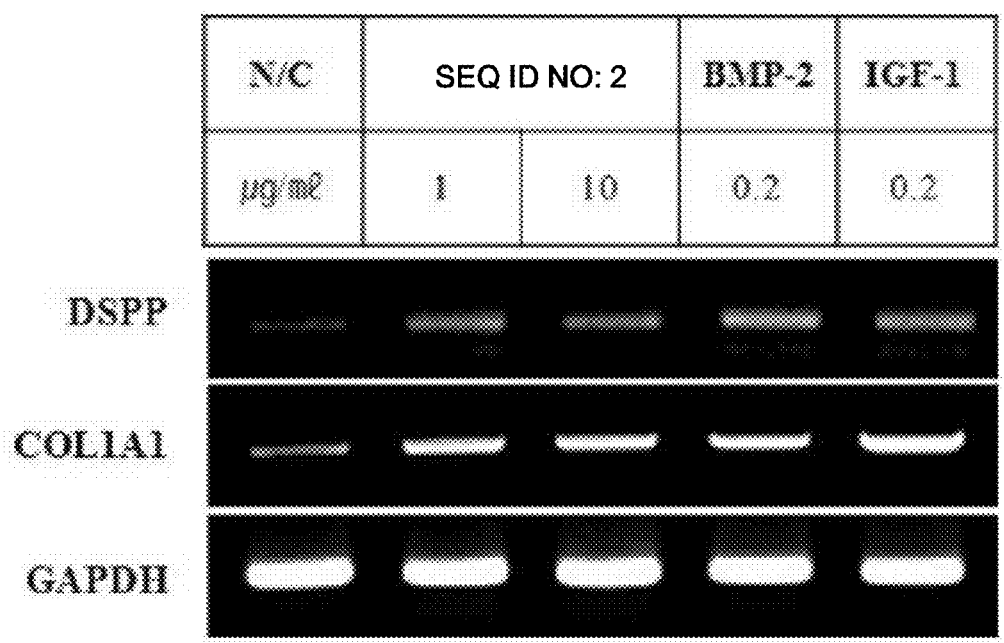
FIG. 8b illustrates results verifying the increases in mRNA expression levels of COL1A1 and DSPP, which are genes related to the activation of periodontal ligament fibroblasts in the treatment with the peptide of SEQ ID NO: 2 prepared by a synthesis example of the present invention.

As results of testing, when the periodontal ligament fibroblasts were treated with the peptides of SEQ ID NO: 1 and SEQ ID NO: 2 at different concentrations, the increases in the mRNA expression levels of alpha-1 type I collagen (COL1A1) and dentin sialophosphoprotein (DSPP), which are cell activity-related genes, were verified (FIGS. 8a and 8b).

Although the present invention has been described in detail with reference to the specific features, it will be apparent to those skilled in the art that this description is only for a certain embodiment and does not limit the scope of the present invention. Thus, the substantial scope of the present invention will be defined by the appended claims and equivalents thereof.

The invention claimed is:

1. A peptide consisting of one amino acid sequence selected from the group consisting of the amino acid sequence of SEQ ID NO: 1 and the amino acid sequence of SEQ ID NO: 2, wherein the N- or C-terminus of the peptide is optionally modified by the presence of a protecting group.

2. The peptide of claim 1, wherein the peptide promotes the proliferation of osteoblasts.

3. The peptide of claim 1, wherein the peptide increases the phosphorylation of Smad1, Smad5, and Smad8, or PI3K and Akt.

4. The peptide of claim 1, wherein the peptide increases the expression of alkaline phosphatase (ALP), collagen type I alpha 1 (COL1A1), and bone sialoprotein (BSP).

5. The peptide of claim 1, wherein the peptide promotes the proliferation of periodontal ligament fibroblasts.

6. The peptide of claim 1, wherein the peptide increases the expression of collagen type I alpha 1 (COL1A1) and dentin sialophosphoprotein (DSPP).

7. A method for treating a bone diseases that would benefit from increased osteoblast proliferation, the method comprising administering a composition containing the peptide of claim 1 as an active ingredient to a subject suffering from the bone disease.

8. A method for treating a periodontal diseases that would benefit from increased periodontal ligament proliferation, the method comprising administering a composition containing the peptide of claim 1 as an active ingredient to a subject suffering from the periodontal disease.

9. The peptide of claim 1, wherein the peptide consists of the amino acid sequence of SEQ ID NO: 1.

10. The peptide of claim 1, wherein the peptide consists of the amino acid sequence of SEQ ID NO: 2.

11. The method of claim 7, wherein the composition comprises a peptide consisting of SEQ ID NO: 1.

12. The method of claim 7, wherein the composition comprises a peptide consisting of SEQ ID NO: 2.

13. The method of claim 8, wherein the composition comprises a peptide consisting of SEQ ID NO: 1.

14. The method of claim 8, wherein the composition comprises a peptide consisting of SEQ ID NO: 2.

15. The peptide of claim 1, wherein the N- or C-terminus of the peptide is modified by the presence of a protecting group.

16. The peptide of claim 15, wherein the protecting group is selected from the group consisting of an acetyl group, a fluorenyl methoxy carbonyl group, a formyl group, a palmitoyl group, a myristyl group, a stearyl group, and polyethylene glycol (PEG).

* * * * *

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: Peptide 1

<400> SEQUENCE: 1

Arg Ser Leu Asn Leu Arg Asp Ser Gln Lys Ser
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Peptide 2

<400> SEQUENCE: 2

Phe Asp Met Gly Ala Tyr Lys Ser Ser Lys
1               5                   10
```